(12) United States Patent
Moctezuma De La Barrera et al.

(10) Patent No.: US 7,771,436 B2
(45) Date of Patent: *Aug. 10, 2010

(54) SURGICAL NAVIGATION TRACKER, SYSTEM AND METHOD

(75) Inventors: Jose Luis Moctezuma De La Barrera, Freiburg (DE); Amir Sarvestani, Freiburg (DE); Markus Jan Boehringer, Alpen (DE); Hans Schoepp, Freiburg (DE); Ulrich Buehner, Denzlingen (DE)

(73) Assignee: Stryker Leibinger GmbH & Co. KG., Freiburg (DE)

( * ) Notice: Subject to any disclaimer, the term of this patent is extended or adjusted under 35 U.S.C. 154(b) by 144 days.

This patent is subject to a terminal disclaimer.

(21) Appl. No.: 11/148,520

(22) Filed: Jun. 9, 2005

(65) Prior Publication Data
US 2005/0288575 A1   Dec. 29, 2005

Related U.S. Application Data

(63) Continuation-in-part of application No. 10/732,553, filed on Dec. 10, 2003.

(51) Int. Cl.
*A61B 17/72* (2006.01)
(52) U.S. Cl. .................. 606/130; 600/424; 73/1.79
(58) Field of Classification Search ............... 600/424, 600/426, 429, 431; 606/130; 382/103; 73/1.79, 73/1.81
See application file for complete search history.

(56) References Cited

U.S. PATENT DOCUMENTS

| 4,383,373 A | 5/1983 | Couturier .................. 33/286 |
|---|---|---|
| 4,567,896 A | 2/1986 | Barnea et al. .............. 128/660 |
| 4,722,056 A | 1/1988 | Roberts et al. ............. 364/413 |
| 5,050,608 A | 9/1991 | Watanabe et al. ........ 128/653 R |
| 5,056,523 A | 10/1991 | Hotchkiss, Jr. et al. ... 128/653 R |
| 5,078,140 A | 1/1992 | Kwoh ....................... 128/653.1 |
| 5,142,930 A | 9/1992 | Allen et al. .................... 74/469 |

(Continued)

FOREIGN PATENT DOCUMENTS

CA    1336451    7/1995

(Continued)

OTHER PUBLICATIONS

Peshkin et al., "Diagramming Registration Connectivity and Structure", Medicine Meets Virtual Reality III, pp. 1-10 (Jan. 1995).

(Continued)

*Primary Examiner*—Brian Casler
*Assistant Examiner*—Amanda Lauritzen
(74) *Attorney, Agent, or Firm*—McCracken & Frank LLP

(57) ABSTRACT

An adapter can be easily used to assist a surgical navigation system to determine the effector axis or the effector plane of a surgical device. The adapter has a body with a geometrical feature, the geometrical feature has a known relation with a navigation tracker device that can be attached to the adapter. When the adapter is held against a surgical device in a non-fixed manner, the effector axis or the effector plane of the device can be tracked by the surgical navigation system. The method includes a calibration method to determine the known relation between the effector axis or the effector plane and the location of the navigation tracker.

30 Claims, 15 Drawing Sheets

U.S. PATENT DOCUMENTS

| | | | |
|---|---|---|---|
| 5,186,174 A | 2/1993 | Schlondorff et al. | 128/653.1 |
| 5,197,476 A | 3/1993 | Nowacki et al. | 128/660.03 |
| 5,198,877 A | 3/1993 | Schulz | 356/375 |
| 5,222,499 A | 6/1993 | Allen et al. | 128/653.1 |
| 5,230,623 A | 7/1993 | Guthrie et al. | 433/72 |
| 5,251,127 A | 10/1993 | Raab | 364/413.13 |
| 5,299,288 A | 3/1994 | Glassman et al. | 395/80 |
| 5,305,203 A | 4/1994 | Raab | 364/413.13 |
| 5,309,913 A | 5/1994 | Kormos et al. | 128/653.1 |
| 5,383,454 A | 1/1995 | Bucholz | 128/653.1 |
| 5,383,454 A | 1/1995 | Bucholz | 128/653.1 |
| 5,389,101 A | 2/1995 | Heilbrun et al. | 606/130 |
| 5,392,384 A | 2/1995 | Tounaki et al. | 395/89 |
| 5,394,875 A | 3/1995 | Lewis et al. | 128/660.09 |
| 5,471,312 A | 11/1995 | Watanabe et al. | 358/296 |
| 5,483,961 A | 1/1996 | Kelly et al. | 128/653.1 |
| 5,494,034 A | 2/1996 | Schlondorff et al. | 128/653.1 |
| 5,517,990 A | 5/1996 | Kalfas et al. | 128/653.1 |
| 5,552,822 A | 9/1996 | Nallakrishnan | |
| 5,564,437 A | 10/1996 | Bainville et al. | 128/774 |
| 5,617,857 A | 4/1997 | Chader et al. | 128/653.1 |
| 5,622,170 A | 4/1997 | Schulz | 128/653.1 |
| 5,662,111 A | 9/1997 | Cosman | 128/653.1 |
| 5,663,795 A | 9/1997 | Rueb | 356/375 |
| 5,676,673 A | 10/1997 | Ferre et al. | 606/130 |
| 5,732,703 A | 3/1998 | Kalfas et al. | 128/653.1 |
| 5,740,222 A | 4/1998 | Fujita et al. | 378/4 |
| 5,748,696 A | 5/1998 | Fujita et al. | 378/4 |
| 5,772,594 A | 6/1998 | Barrick | 600/407 |
| 5,787,886 A | 8/1998 | Kelly et al. | 128/653.1 |
| 5,848,126 A | 12/1998 | Fujita et al. | 378/195 |
| 5,848,967 A | 12/1998 | Cosman | 600/426 |
| 5,851,183 A | 12/1998 | Bucholz | 600/425 |
| 5,876,325 A | 3/1999 | Mizuno et al. | 600/102 |
| 5,891,034 A | 4/1999 | Bucholz | 600/426 |
| 5,921,992 A * | 7/1999 | Costales et al. | 606/130 |
| 5,954,648 A | 9/1999 | Van Der Brug | |
| 5,967,982 A | 10/1999 | Barnett | 600/429 |
| 5,987,960 A * | 11/1999 | Messner et al. | 73/1.79 |
| 5,999,837 A | 12/1999 | Messner et al. | 600/407 |
| 6,006,126 A | 12/1999 | Cosman | 600/426 |
| 6,021,343 A | 2/2000 | Foley et al. | 600/429 |
| 6,081,336 A | 6/2000 | Messner et al. | |
| 6,112,113 A | 8/2000 | Van Der Brug et al. | 600/427 |
| 6,167,295 A | 12/2000 | Cosman | 600/426 |
| 6,205,411 B1 | 3/2001 | DiGioia, III et al. | 703/111 |
| 6,236,875 B1 | 5/2001 | Bucholz et al. | |
| 6,266,551 B1 | 7/2001 | Osadchy et al. | 600/424 |
| 6,273,896 B1 * | 8/2001 | Franck et al. | 606/130 |
| 6,275,725 B1 | 8/2001 | Cosman | 600/426 |
| 6,282,437 B1 | 8/2001 | Franck et al. | 600/429 |
| 6,285,902 B1 | 9/2001 | Kienzle, III et al. | 600/427 |
| 6,298,262 B1 | 10/2001 | Franck et al. | 600/426 |
| 6,306,126 B1 | 10/2001 | Moctezuma | 606/1 |
| 6,335,617 B1 | 1/2002 | Osadchy et al. | 324/202 |
| 6,370,411 B1 | 4/2002 | Osadchy et al. | 600/372 |
| 6,377,839 B1 * | 4/2002 | Kalfas et al. | 600/426 |
| 6,428,547 B1 | 8/2002 | Vilsmeier et al. | 606/130 |
| 6,434,507 B1 * | 8/2002 | Clayton et al. | 702/152 |
| 6,442,416 B1 | 8/2002 | Schultz | 600/429 |
| 6,478,802 B2 * | 11/2002 | Kienzle et al. | 606/130 |
| 6,497,134 B1 | 12/2002 | Faul et al. | |
| 6,511,418 B2 | 1/2003 | Shahidi et al. | |
| 6,514,259 B2 | 2/2003 | Picard et al. | 606/88 |
| 6,517,478 B2 | 2/2003 | Khadem | |
| 6,542,770 B2 * | 4/2003 | Zylka et al. | 600/424 |
| 6,584,339 B2 | 6/2003 | Galloway, Jr. et al. | |
| 6,675,040 B1 * | 1/2004 | Cosman | 600/427 |
| 6,697,664 B2 * | 2/2004 | Kienzle, III et al. | 600/427 |
| 6,725,080 B2 * | 4/2004 | Melkent et al. | 600/424 |
| 6,973,202 B2 * | 12/2005 | Mostafavi | 382/103 |
| 7,008,430 B2 * | 3/2006 | Dong et al. | 606/80 |
| 7,029,477 B2 * | 4/2006 | Grimm | 606/88 |
| 7,043,961 B2 * | 5/2006 | Pandey et al. | 73/1.81 |
| 7,166,114 B2 * | 1/2007 | Moctezuma De La Barrera et al. | 606/130 |
| 7,213,598 B2 * | 5/2007 | Zeiss et al. | 128/897 |
| 2001/0027271 A1 * | 10/2001 | Franck et al. | 600/426 |
| 2001/0034530 A1 | 10/2001 | Malackowski et al. | 606/130 |
| 2001/0036245 A1 | 11/2001 | Kienzle, III et al. | 378/4 |
| 2002/0016599 A1 * | 2/2002 | Kienzle et al. | 606/130 |
| 2002/0077540 A1 | 6/2002 | Kienzle, III | 600/424 |
| 2002/0077543 A1 | 6/2002 | Grzeszczuk et al. | 600/424 |
| 2002/0077544 A1 | 6/2002 | Shahidi | 600/424 |
| 2002/0133160 A1 | 9/2002 | Axelson, Jr. et al. | 606/88 |
| 2002/0133161 A1 | 9/2002 | Axelson, Jr. et al. | 606/88 |
| 2002/0133162 A1 | 9/2002 | Axelson, Jr. et al. | 606/88 |
| 2002/0133163 A1 | 9/2002 | Axelson, Jr. et al. | 606/88 |
| 2003/0209096 A1 | 11/2003 | Pandey et al. | |
| 2005/0228270 A1 * | 10/2005 | Lloyd et al. | 600/424 |
| 2006/0058644 A1 * | 3/2006 | Hoppe et al. | 600/423 |
| 2006/0122630 A1 * | 6/2006 | Daum et al. | 606/130 |
| 2006/0200025 A1 * | 9/2006 | Elliott et al. | 600/424 |
| 2007/0175489 A1 * | 8/2007 | Moctezuma De La Barrera et al. | 128/898 |
| 2007/0208352 A1 * | 9/2007 | Henderson et al. | 606/130 |
| 2008/0039868 A1 * | 2/2008 | Tuemmler et al. | 606/130 |
| 2008/0071140 A1 * | 3/2008 | Gattani et al. | 600/117 |
| 2008/0249394 A1 * | 10/2008 | Giori et al. | 600/407 |
| 2008/0269602 A1 * | 10/2008 | Csavoy et al. | 600/426 |

FOREIGN PATENT DOCUMENTS

| | | |
|---|---|---|
| EP | 326 768 A2 | 12/1988 |
| EP | 469 966 B1 | 7/1991 |
| JP | 57-21250 | 2/1982 |
| JP | 61-25531 | 2/1986 |
| JP | 61-31129 | 2/1986 |
| JP | 1-245108 | 9/1989 |
| JP | 03-057466 | 3/1991 |
| JP | 05-049644 | 3/1993 |
| JP | 51-11886 | 5/1993 |
| JP | 07-194616 | 8/1995 |
| JP | 07-236633 | 9/1995 |
| JP | 07-323035 | 12/1995 |
| JP | 07-328016 | 12/1995 |
| JP | 08-010266 | 1/1996 |
| JP | 08-38507 | 2/1996 |
| WO | WO 91/04711 | 4/1991 |
| WO | WO 91/07726 | 5/1991 |
| WO | WO 92/06645 | 4/1992 |
| WO | WO 94/23647 | 10/1994 |
| WO | WO 94/24933 | 11/1994 |
| WO | WO 96/11624 | 4/1996 |
| WO | WO 96/32059 | 10/1996 |
| WO | WO 97/15234 | 5/1997 |
| WO | WO 97/29678 | 8/1997 |

OTHER PUBLICATIONS

Ahlers et al., "Calibration Requirements and Procedures for a Monitor-Based Augmented Reality System", European Computer Industry Research Centre, pp. 1-32 (Jul. 6, 1995).

Viergever et al. "An Overview of Medical Image Registration Methods", Imaging Science Department, Imaging Center Utrecht, pp. 1-22.

Stulberg et al., "A Computer-Assisted Total Knee Replacement Surgical System Using a Calibrated Robot", Northwestern University, pp. 1-28.

Peshkin et al, "Complete Parameter Identification of a Robot From Partial Pose Information" Northwestern University, pp. 1-26.

Rose et al, "Object Calibration for Augmented Reality", European Computer-Industry Research Centre GmbH, pp. I-III, 1-18 (Aug. 1995).

Bergmann et al., "Calibration of Tracking Systems in a Surgical Environment", IEEE Transactions on Medical Imaging, pp. 1-6 (Oct. 1988).

Jiang et al., "Interactive Intraoperative Localization Using an Infrared-Based System", Wayne State University, pp. 84-88 (Oct. 1993).

Reinhardt et al., "Micro-Stereometry: A Frameless Computerized Navigating System for Open Microsurgery", Computerized Medical Imaging and Graphics vol. 18, pp. 229-233 (1994).

Long et al., "An Optical 3D Digitizer for Frameless Stereotactic Surgery", IEEE Computer Graphics and Applications pp. 55-64 (1996).

Kadi et al., "Computer-Assisted Neurosurgery System: Wayne State University Hardware and Software Configuration", Computerized Medical Imaging and Graphics, vol. 18, No. 4, pp. 257-271 (1994).

Bucholz et al., "Frameless Stereotactic Ultrasonograph Computerized Medical: Method and Applications", Imaging and Graphics, vol. 18, No. 4, pp. 235-246 (1994).

Phillips et al., "Image Guided Orthopaedic Surgery Design and Analysis", Transactions of the Institute of Measurement and Control vol. 17, No. 5, pp. 251-264 (1995).

Office Action in U.S. Appl. No. 10/732,553 dated Oct. 7, 2008.

* cited by examiner

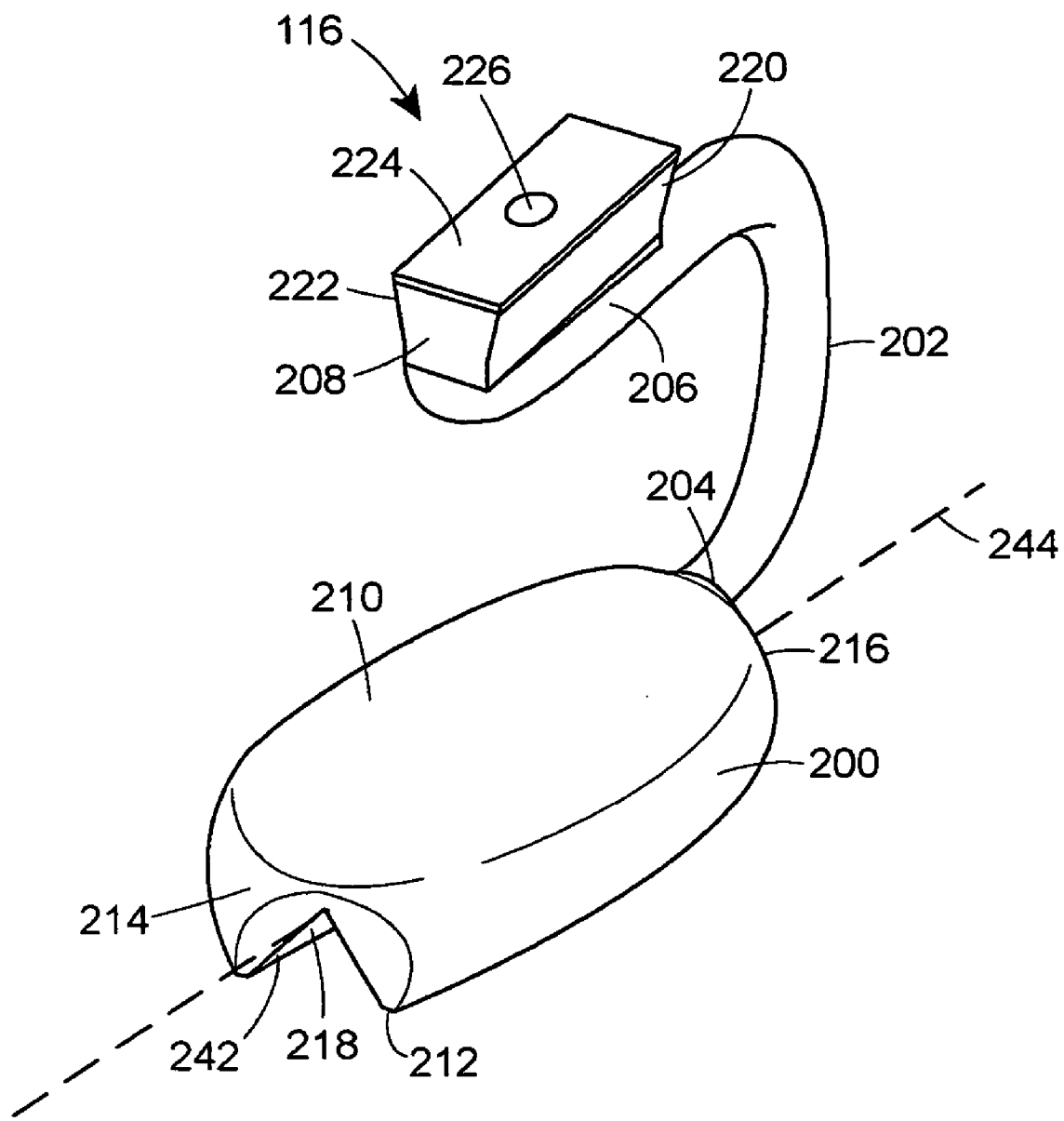

SURGICAL NAVIGATION TRACKER, SYSTEM AND METHOD

CROSS REFERENCE TO RELATED APPLICATIONS

This application is a continuation-in-part of application Ser. No. 10/732,553, filed Dec. 10, 2003.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

This invention relates generally to a surgical navigation system. More particularly, this invention relates to a system, a tracking device, and an adapter to assist the surgical navigation system orient a surgical instrument or device relative to a body of a patient.

2. Description of the Background of the Invention

The use of image guided surgical navigation systems for assisting surgeons during surgery is quite common. Such systems are especially widely used during procedures requiring precise location of instruments such as neurosurgery and more recently orthopedic surgery. Typical surgical navigation systems utilize specially developed tools that include built in tracking devices or tool and adapter combinations that allow a tracking device to be affixed to a surgical tool. These tracking devices allow a surgeon to see the position and/or orientation of the surgical tool overlaid on a monitor in conjunction with a preoperative image or an intraoperative image of the patient. Preoperative images are typically prepared by MRI or CT scans, while intraoperative may be prepared by using a fluoroscope, low level x-ray or any similar device. The tracking devices typically use a plurality of optical emitters that can be detected by the navigation system to determine the position and orientation of the surgical instrument.

One of the main challenges with present surgical navigation systems is the time required to properly apply and calibrate the tracking devices to work with conventional surgical instruments. Raab U.S. Pat. No. 5,251,127 teaches a computer aided surgery apparatus for positioning a surgical instrument that employs a computer driven instrumented linkage attached to a surgical instrument. Foley et al. U.S. Pat. No. 6,021,343 discloses a handheld surgical instrument with a tracking device that requires pre-dedicated and specially made surgical tool connections. Kienzle, III et al. U.S. patent application No. 2001/0036245 is directed towards a surgical tool with integrated localizing emitters for superimposing a representation of the tool over an image of a body in surgery.

Dedicated adapters for surgical instruments are expensive and time consuming to develop. Additionally, most of these devices require calibration of the surgical instrument after the tracking device has been attached in order to determine the transformation between the tracking device and an axis of the instrument. Moctezuma de la Barrera et al. U.S. patent application Ser. No. 10/246,599 teaches a surgical instrument fixedly attached to a tracking device, wherein the calibration of the position and orientation of the surgical instrument is accomplished by a separate device. In addition, for orthopedic surgery, it is sometimes necessary to apply force to the surgical tool. This force can damage the precision tracking device, such as damaging the electronics, the LEDs, or disturbing the calibration of the tracking device, if the tracking device is firmly attached to the tool when the force is applied. The present device allows a surgeon to track the orientation of the effector axis or effector plane of a wide range of instruments without the need to either calibrate the tool tracker combination or fixedly attaching a tracking device to a surgical instrument. In addition, the devices of this invention can be used to place items in the body in precise locations. One example of devices that must be properly placed are shunts that are place in the brain to drain fluid.

SUMMARY OF THE INVENTION

The present invention is also directed towards a method for orienting a surgical device. This method includes the steps of coupling by a user's hand a navigation tracker to a surgical device that has an effector axis in a movable manner using a geometrical feature associated with the navigation tracker. The navigation tracker is capable of communicating with a navigation system, and there is a known relation between the navigation tracker and the effector axis. Another step is calculating orientation data for the effector axis of the surgical device from the known relation between the navigation tracker to the effector axis. The calculating step is performed while the surgical device is moving longitudinally along the geometrical feature and movably coupled to the navigation tracker by the user's hand. Lastly, the method includes the step of displaying the orientation data for the effector axis of the surgical device on a display unit of the surgical navigation system so that when the surgical device is used with the navigation system, the orientation of the effector axis of the surgical device can be tracked by the surgical navigation system.

The present invention is further directed towards an adapter to attach a navigation tracker to a surgical device. The adapter has a body and a connector having a first end attached to the body and a second end. An interface attached to the second end to enable a navigation tracker to be attached to the adapter. The body has geometrical features to enable a surgical device to be non-fixedly coupled to the body.

Other aspects and advantages of the present invention will become apparent upon consideration of the following detailed description.

BRIEF DESCRIPTION OF THE DRAWINGS

FIG. 2 is an isometric view of one embodiment of the adapter of the present invention;

DETAILED DESCRIPTION OF THE PREFERRED EMBODIMENTS

Figure 1:
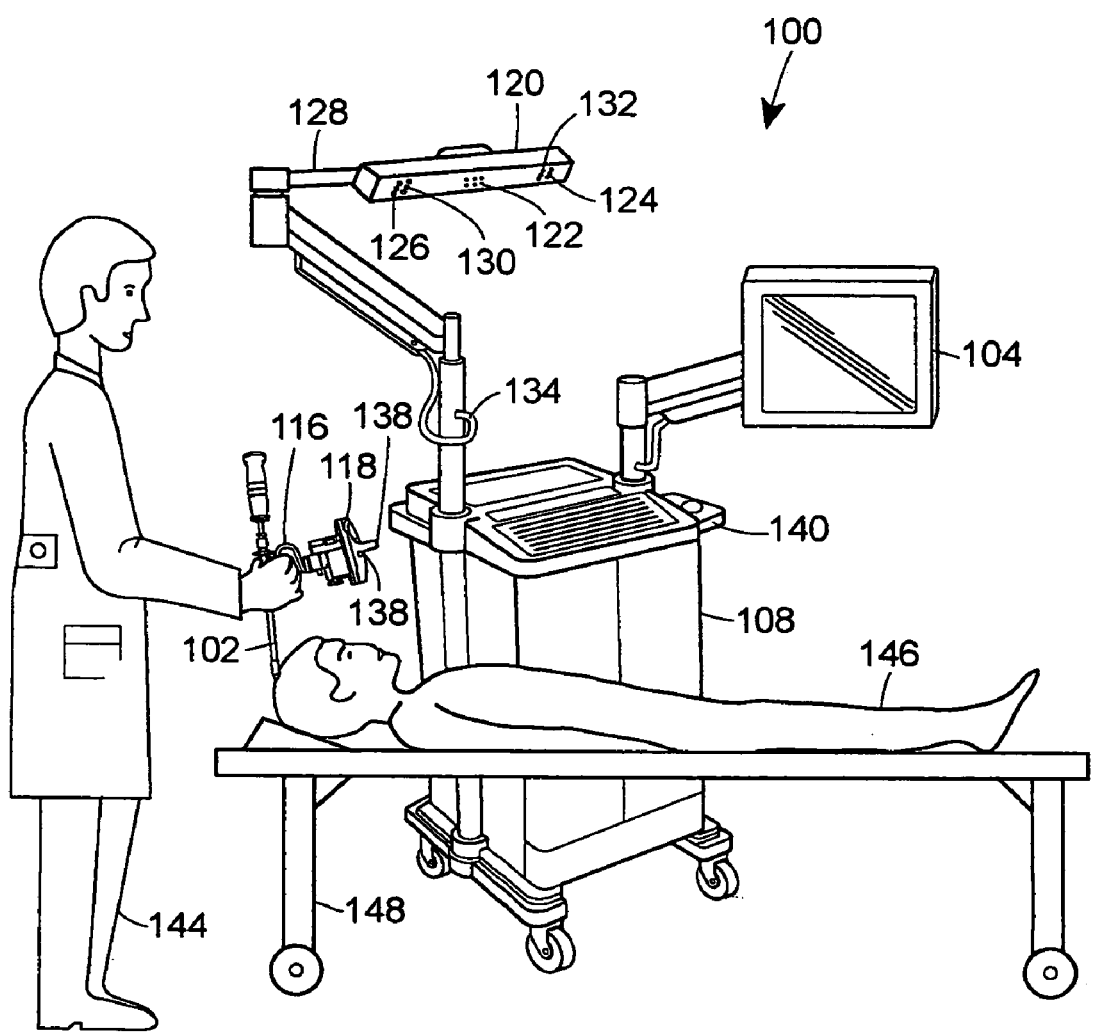
FIG. 1 is a schematic view of the surgical navigation system.
Figure 1A:
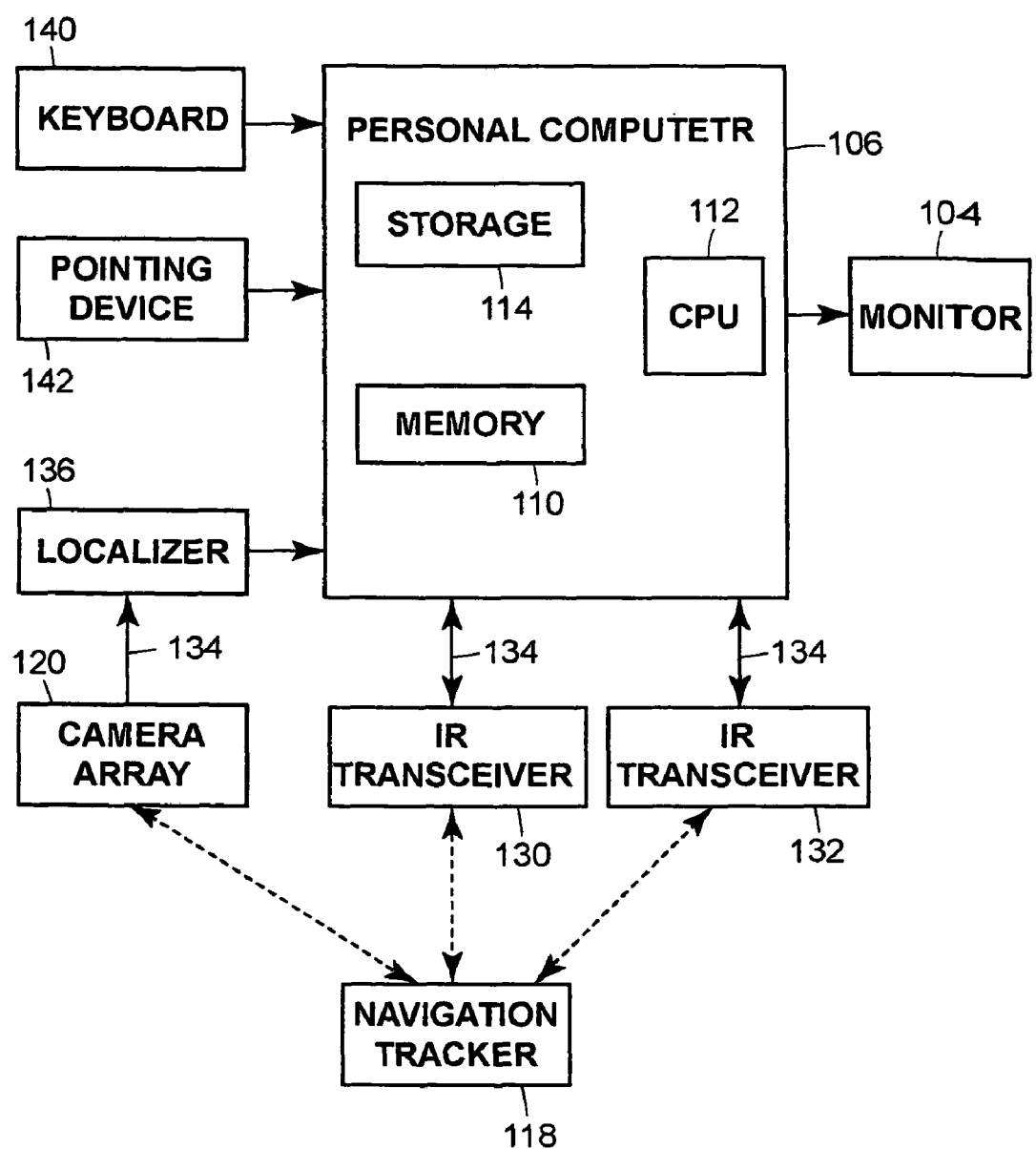
FIG. 1A is a block diagram of the surgical navigation system of FIG. 1.
Figure 3:
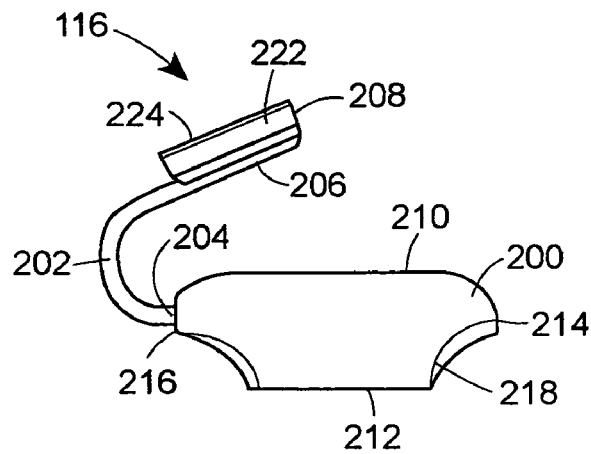
FIG. 3 is a side elevational view of the adapter of FIG. 2.
Figure 4:
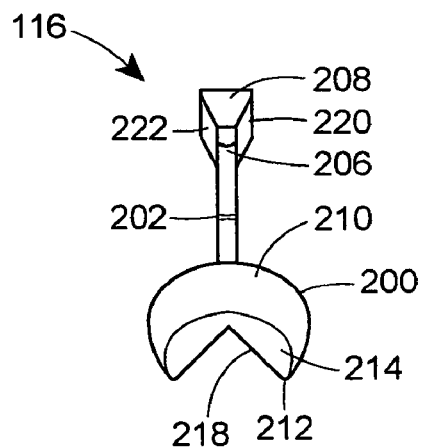
FIG. 4 is an end elevational view of the adapter of FIG. 2.
Figure 5:
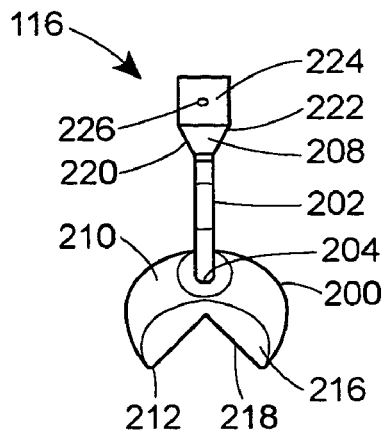
FIG. 5 is an end elevational view of the adapter of FIG. 2 from the end opposite FIG. 4.

With reference to the drawings, the present invention is directed towards a surgical navigation system 100 for orienting a surgical instrument 102. FIGS. 1 and 1A are a schematic view and block diagram of the surgical navigation system 100 that includes a display unit 104, a computer system 106 and a camera array 120. The computer system 106 may be housed in a moveable cart 108. The computer system 106 may be any type of personal computer having a memory unit 110, a CPU 112, and a storage unit 114. The display unit 104 can be any conventional display usable with a personal computer.

The camera array 120 is adapted to track a navigation tracker 118. The camera array 120 is further adapted to transmit data between the navigation tracker 118 and computer system 106 representing the orientation of the surgical instrument 102. In a preferred embodiment, the data is transmitted wirelessly between the navigation tracker 118 and the computer system 106. Alternatively, a system that uses wires to transmit data between the navigation tracker 118 and the computer system 106 can be used.

With reference to FIG. 1, the camera array 120 includes a first camera 122, a second camera 124, and a third camera 126. In a preferred embodiment, the first, second and third cameras, 122, 124, and 126, are three CCD cameras adapted to detect the position of infrared signals (IR) generated by the navigation tracker 118.

The camera array 120 should be mounted in a stationary position with a sufficient line of sight to the operating room. In one embodiment, the camera array 120 is mounted on a rotatable arm 128 attached to the movable cart 108. In another embodiment, the camera array 120 may be mounted onto an operating room wall (not shown) or onto other convenient surfaces or locations.

At least one infrared transceiver is used to communicate data to and from the navigation tracker 118. In the preferred embodiment, the sensor array 120 includes a first transceiver 130 and a second transceiver 132 located apart from each other. It should be noted that while both the navigation tracker 118 and the transceivers, 130 and 132, may communicate via infrared signals, those skilled in the art will realize other wireless technologies such as radio frequency signals may be used as well as hardwired systems, so called electromagnetic communication.

The camera array 120 is connected via a cable 134 to a localizer 136 or in some instances directly to the computer. The localizer 136 cooperates with the camera array 120 to identify the location of a plurality of LED's 138 on the navigation tracker 118 within the line of sight of the sensor array 120. The first, second, and third cameras, 122, 124, and 126, contain their own orientation data and transmit that data and the orientation data from the plurality of LED's 138 to the localizer 136. In one embodiment, the localizer 136 converts the raw orientation data into the orientation of individual LED's of the plurality of LED's 138 and transmits this information to the computer system 106. In another embodiment, the localizer 136 converts the raw data into the orientation of the surgical instrument 102 and transmits this information to the computer system 106. In a further embodiment, a software program in the computer system 106 can convert the raw data into the orientation of the surgical instrument 102. In all embodiments, the conversion of the raw data is well known to one skilled in the art and need not be further discussed. The computer system 106 may be controlled remotely by control buttons (not visible) located on the navigation tracker 118. The computer system 106 also includes a keyboard 140 and a pointing device 142, such as a mouse or any alternative input means for operating the computer system 106. The surgical navigation system 100 is used by a surgeon 144 during a procedure on a patient 146. Preferably, the patient 146 is located on a surgical bed or a table 148.

The preferred embodiment of the present invention includes a surgical instrument 102 non-fixedly coupled to an adapter 116. The adapter 116 is, however, coupled to a navigation tracker 118 that is in communication with the sensor array 120 and transceivers 130 and 132. The use of navigation trackers in combination with sensor arrays and transceivers are well known in the art. A more detailed description of such surgical navigation systems are contained in U.S. patent application Ser. No. 10/246,599 filed Sep. 18, 2002, the disclosure of which is hereby incorporated by reference.

While the present invention is described using an active optical surgical navigation system, the system, method and adapters of the present invention can also be used with other surgical navigation technologies and systems, such as passive optical systems, magnetic based systems, inertial navigation based systems, combination systems, and the like.

FIGS. 2 to 5 show one embodiment of the present invention. The adapter 116 includes a body 200, a connector 202 having a first end 204 attached to the body 200 and a second end 206 attached to a docking structure 208. The body 200 has a first side 210, a second side 212, a first end 214, and a second end 216. The second side 212 defines a geometrical feature 242. In the case shown in FIGS. 2 to 5, the geometrical feature 242 is a channel 218 extending along the entire length of the second side 212. The geometrical feature 242 of the adapter 116 will define an adapter axis 244. Knowledge of the location of the adapter axis 244 relative to the location of the navigation tracker 118 will be useful for those situations where only the angle of the instrument needs to be tracked by the surgical navigation system. The docking structure 208 has a first beveled side 220, a second beveled side 222 and a surface 224 that has a locking detent 226. The docking structure 208 engages cooperating structure on the navigation tracker 118 as discussed hereinafter.

Figure 6:
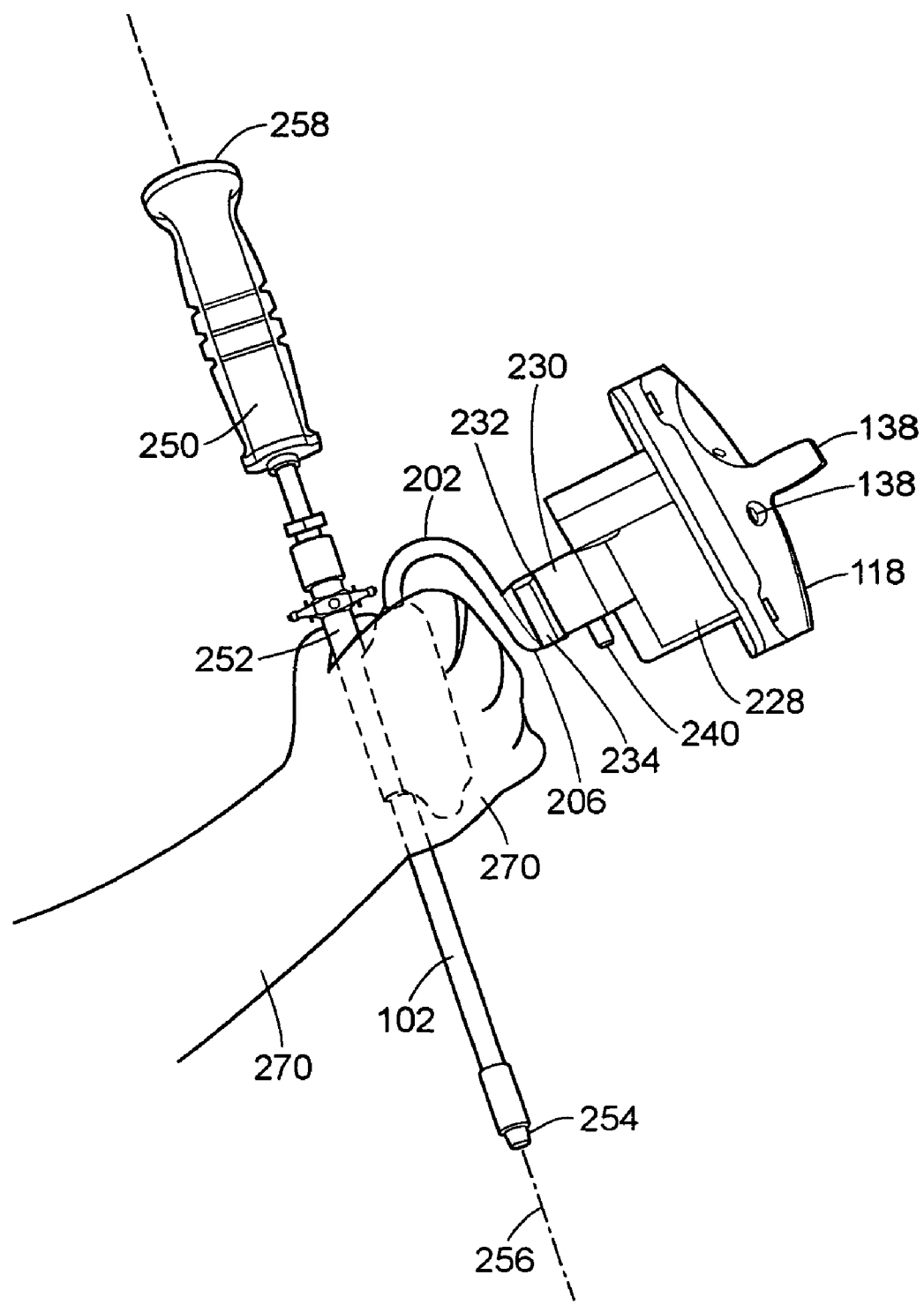
FIG. 6 is an isometric view of the surgical instrument being held by a hand in a non-fixed relationship with adapter of FIG. 2 connected to a navigation tracker.
Figure 7:
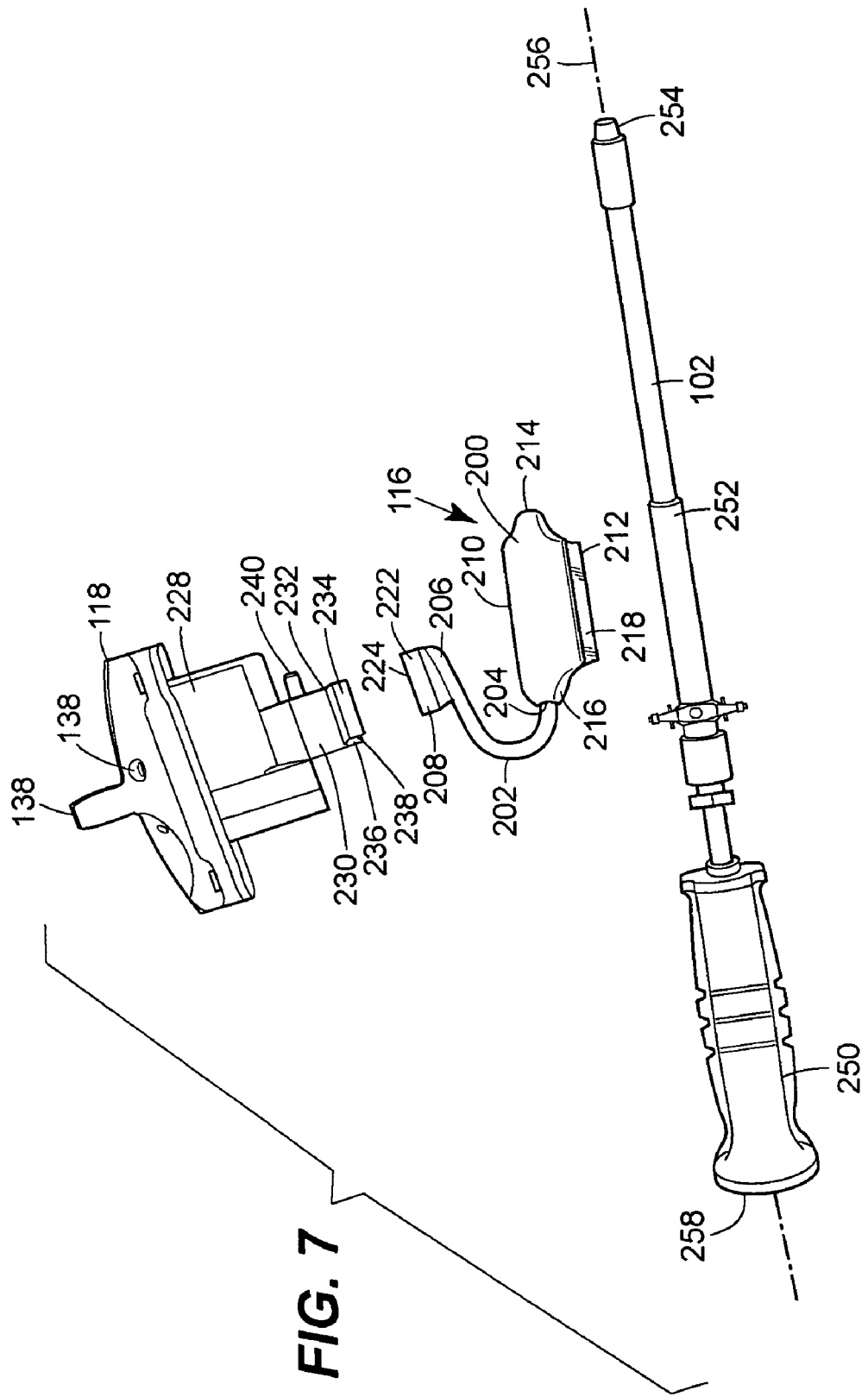
FIG. 7 is an exploded view of the surgical instrument, adapter, and navigation tracker of FIG. 4.

FIGS. 6 and 7 show the embodiment of FIG. 2 in an in-use situation on the surgical instrument 102 with a tracking device 118. The tracking device 118 is a known device and has a body 228. Mounted in fixed positions on the body 228 are the LEDs 138. Also depending from the body 228 is a mounting bracket 230 having a distal end 232. The distal end 232 is attached to a pair of walls 234 and 236. The walls 234 and 236 are shaped to form a slit 238 that will slide over the first and second beveled sides 220 and 222. The slit 238 will mate in a precision mating arrangement with the docking structure 208. In the interior of the slit 238 is a spring loaded locking structure (not shown) that will allow the surface 224 to slide within the slit 238 until the locking structure reaches the locking detent 226. At this time, the spring will bias the locking structure into the locking detent 226 and firmly hold the tracking device 118 in fixed relationship with the adapter 116. To remove the tracking device 118 from the adapter, a button 240 is pushed that will release the locking structure within the slit 238 and allow the tracking device to be removed from the adapter 116.

The surgical instrument 102 has a handle 250, a shaft 252, an adapter tip 254 to hold various devices in position, an instrument axis 256 and a striking surface 258. The particular instrument 102 shown in FIGS. 1, 6 and 7 is an impactor used to insert implants attached to the adapter tip 254 during orthopedic surgery. Because the instrument 102 will be struck with a hammer or other impacting device on the impacting surface 258, it is desirable to navigate the instrument 102 into proper position and then remove the delicate tracking device before the instrument 102 is struck. FIG. 6 shows a surgeon's hand 270 holding the adapter 116 in a non-fixed coupling with the instrument 102. When the term non-fixed coupling is used in this specification and in the attached claims, it means the adapter 116 is held in a reproducible relation to a surgical tool, such as instrument 102, but is easily removable when the holding force is removed from the adapter. This term includes the situation where the adapter 116 is held in proximity to the instrument 102 by a user's hand and will fall away from the instrument 102 if the hand pressure is removed. Because the shaft 252 has a surface that is co-axial with the instrument axis 256, the adapter 116 can be moved along the shaft 252 and the relation between the tracker 118 and the instrument axis 256 remains the same.

Figure 8:
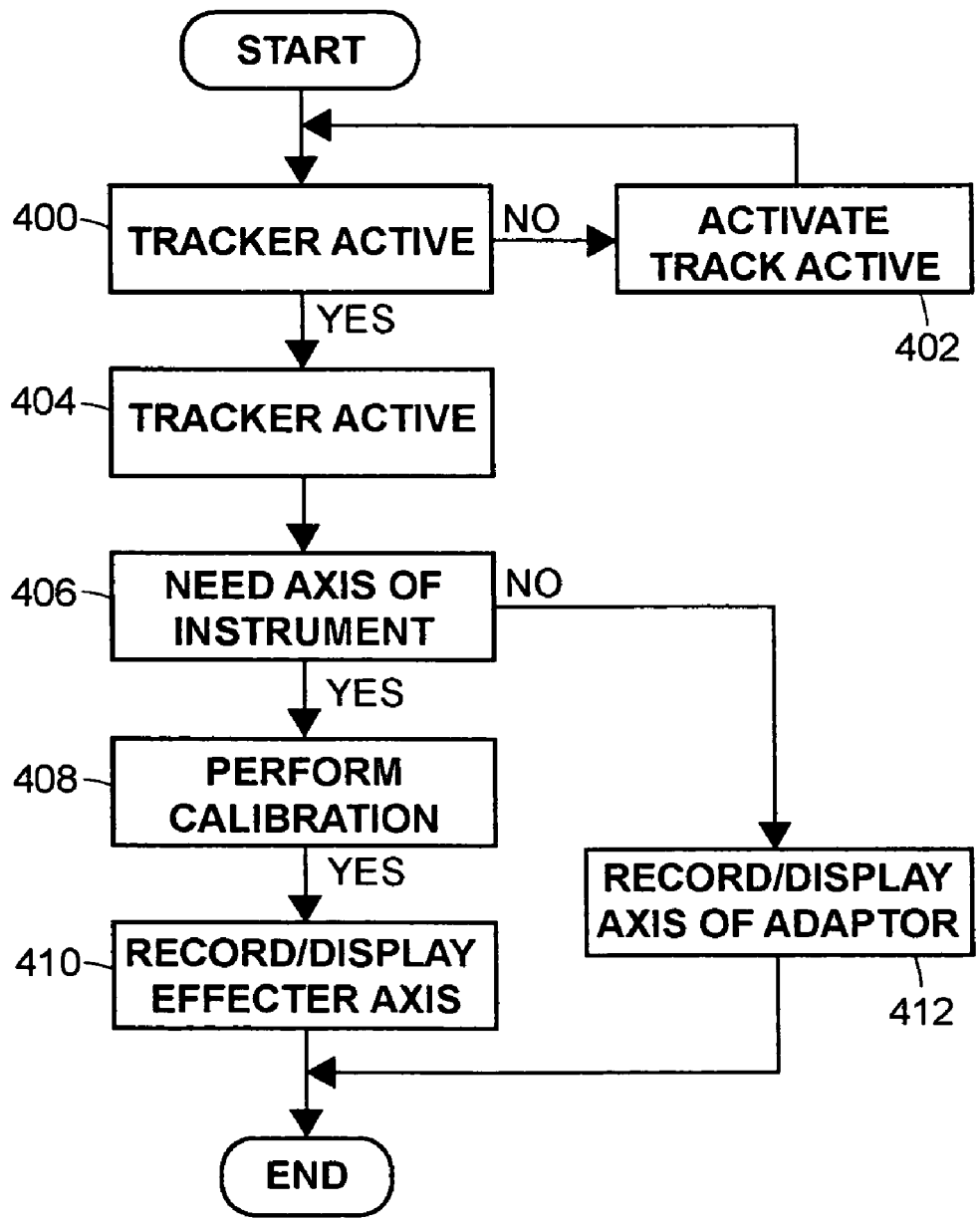
FIG. 8 is a block diagram of a computer program embodying one embodiment of the method of the present invention.

FIG. 8 is a block diagram of a computer program embodying the method of the present invention. The program begins at a block 400 that determines if the navigation tracker 118 has been activated. If the navigation tracker 118 is not active, the program branches to a block 402, which displays a message to prompt a user to activate the navigation tracker 118. The program returns to the block 400 and waits until the surgical navigation system 100 receives a signal that the navigation tracker 118 is active. When the surgical navigation system 100 determines that the navigation tracker 118 is active, the control passes to a block 404 that displays a message that the navigation tracker 118 is active and control then passes to a block 406 that determines if the user needs to identify the effector axis of the surgical instrument. If the user responds "yes", then control passes to a block 408 that calibrates the particular instrument-adapter-tracker combination. The block 408 instructs the user to rotate the tool-adapter-tracker combination about the effector axis. The block 408 will determine the location of the tracker 118 as the combination is rotated and will calculate the relation between the tracker 118 and the effector axis. In a similar manner, the block 408 can instruct a user to invert a tool-adapter-tracker combination where the tool has an effector plane. In this case, the plane of the tool is first placed on a fixed location and the location of the tracker is determined. The tool is then inverted and the plane of the tool is placed at the same location. The location effector plane of the tool relative to the tracker is the distance between the first and second locations of the tracker. Control then passes to a block 410 that records the relation between the tracker 118 and the effector axis or effector plane in the memory unit 110 and displays the effector axis or plane on the display unit 104. If the user responds "no" in block 406, control passes to a block 412 that records the axis of the adapter 116 in memory unit 110 and displays the adapter axis on the display unit 104. These methods of quickly calibrating the tool-adapter-tracker combination in the block 408 are acceptable for applications requiring knowledge only of the location or the effector axis or the effector plane and the knowledge of the location of the tip or working surface of the tool is not required. In situations where only the relevant angle of the tool is required, there is no need to calibrate the adaptor and tracker to the effector axis of the instrument because the effector axis of the instrument will be parallel to the axis of the adapter 116.

Figure 9:
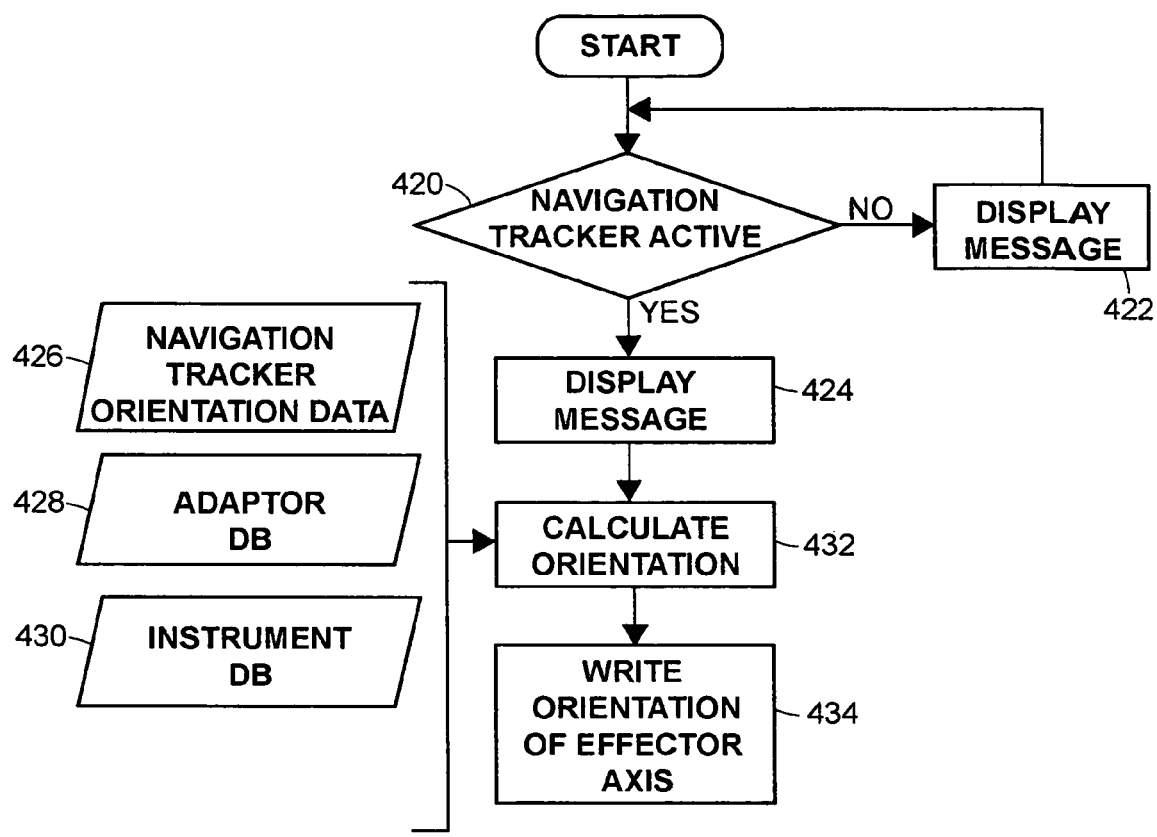
FIG. 9 is a block diagram of a computer program embodying a further embodiment of the method of the present invention.

FIG. 9 is a block diagram of another computer program embodying the method of the present invention. This embodiment uses a series of databases that have been previously created relative to the potential tools, adapters and trackers that might be used with the surgical navigation system 100. The program begins at a block 420 that determines if the navigation tracker 118 has been activated. If the navigation tracker 118 is not active, the program branches to a block 422, which displays a message to prompt a user to activate the navigation tracker 118. The program returns to the block 420 and waits until the surgical navigation system 100 receives a signal that the navigation tracker 118 is active. When the surgical navigation system 100 determines that the navigation tracker 118 is active, the control passes to a block 424 that displays a message that the navigation tracker 118 is active and control then passes to a block 432 that calculates the orientation of the effector axis. This surgical navigation system 100 determines the location and orientation of the navigation tracker 118 and the block 426 stores this data in the memory unit 110.

It is envisioned that there will be a number of different configurations of the adapter 116. As such, the distance between the navigation tracker 118 and the effector axis of a particular surgical instrument may vary depending on the type of adapter 116 used, and the type of instrument used. Each type of adapter 116 can be encoded with a specific identifier that can be entered into the surgical navigation system 100 and similarly the surgical navigation system 100 can prompt the entry of coding information for particular tools that are used. Alternatively, these tools or instruments may also be able to directly communicate with the surgical navigation system 100 and self identify the tool and/or the adapter. A block 428 is a database of stored dimensions for a number of adapters. The same may be done for each possible surgical instrument that can be used with the surgical navigation system 100. A block 430 is a database of stored dimensions for various surgical instruments and their corresponding effector axes. The surgical navigation system 100 also will allow a user to manually input data for an adapter or a tool that is not found within the respective database. It is desirable, but not necessary, that the navigation tracker 116 be a smart instrument that can relate its own configuration data to the surgical navigation system when the navigation tracker 118 is activated by the surgical navigation system 100. Once the surgical navigation system 100 knows the identity of the particular adapter 116 and the surgical instrument 102, the corresponding databases 428 and 430 are queried for the dimensions of the interface and channel configuration, the dimensions of the surgical instrument and its effector axis. This data may be manually entered or stored before or after the navigation tracker 118 is activated. The surgical navigation system 100 identifies the dimensions of the navigation tracker 118 in a conventional manner.

The program then proceeds to calculate the orientation of the effector axis of the surgical instrument 102 from the stored data of the navigation tracker 118 in block 426 and the stored data obtained from the blocks 428 and 430. A block 432 calculates the orientation in a conventional fashion using algorithms that are well known and recognized by those skilled in the art. A block 434 stores the orientation data in the memory unit 110, and displays the orientation information on the display 104 for use by the operator 144. Combinations of the uses of databases for various components and the kinematic approach shown in FIG. 8 can also be used.

Figure 10:
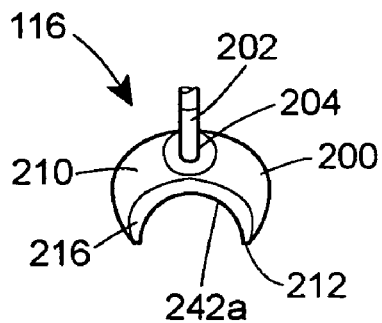
FIG. 10 is an end elevational view similar to FIG. 5 of an alternative embodiment of the adapter of the present invention.
Figure 11:
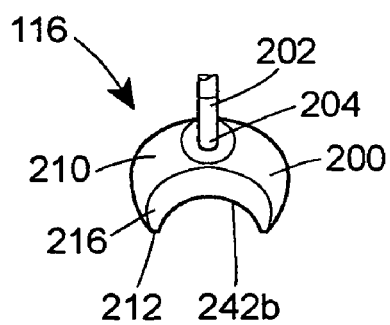
FIG. 11 is an end elevational view similar to FIG. 5 of a further alternative embodiment of the adapter of the present invention.
Figure 12:
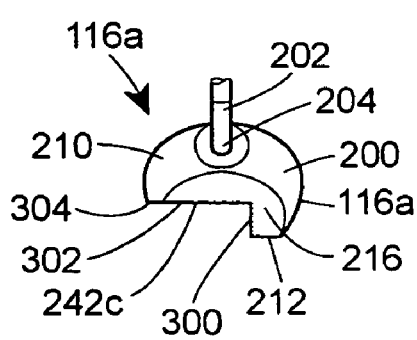
FIG. 12 is an end elevational view similar to FIG. 5 of an additional alternative embodiment of the adapter of the present invention.
Figure 13:
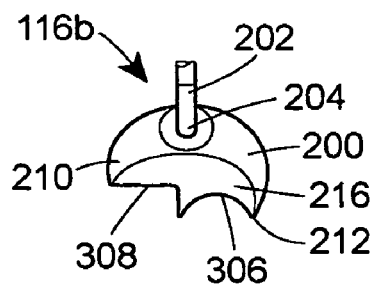
FIG. 13 is an end elevational view similar to FIG. 5 of a still further alternative embodiment of the adapter of the present invention.

FIGS. 10, 11, 12, and 13 are alternative shapes of the geometrical feature 242 in FIG. 2 for the adapter 116. The feature 242a in FIG. 10 is circular, while the feature 242b in FIG. 11 is elliptical. In FIG. 12, the second side 212 of the adapter 116 has a wall 300 that is generally perpendicular to a surface 302 that extends from the wall 300 to a periphery 304 of the body 200. The wall 300 and the surface 302 form an "L" shaped geometrical feature 242c. The adapter 116a as shown in FIG. 12 is adapted to be used with surgical tools or instruments having a rectangular cross section and the open end of the surface 302 enables the adapter 116a as shown in FIG. 12 to be used with a wider variety of tools than if the adapter 116a had a rectangular channel. The primary difference between this embodiment and the others previously mentioned is that in addition to an upward force exerted against the surgical instrument 102 to hold the surgical instrument 102 against the surface 302 of the geometrical feature 242c, a lateral force is also applied to hold the surgical instrument 102 against the wall 300 of the geometrical feature 242c. For instance, the adapter 116a could be used with an instrument or tool that had a handle or shaft wider than the width of the adapter 116a. FIG. 13 shows an adapter 116b that has multiple geometric features 306 and 308. This arrangement allows the adapter 116b to be used with different tools without having to remove the navigation tracker from the adapter 116b.

Figure 14:
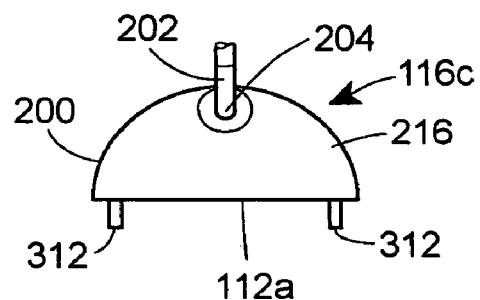
FIG. 14 is an end elevational view similar to FIG. 5 of another further embodiment of the adapter of the present invention.
Figure 15:
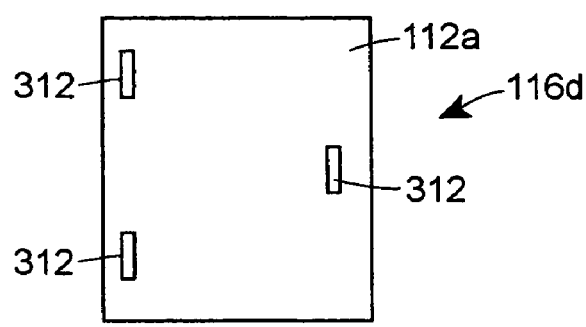
FIG. 15 is a bottom plan view of the adapter of FIG. 14.

FIGS. 14 and 15 show a further embodiment of the geometrical feature 242. An adapter 116c has a bottom surface 112a and three depending lugs 312. The number of depending lugs is not particularly critical and any number more than 2 can be used. For instance, two longer lugs can be sufficient to hold the adapter in position on the instrument 102, or four or more smaller lugs can be used to the same effect.

Figure 16:
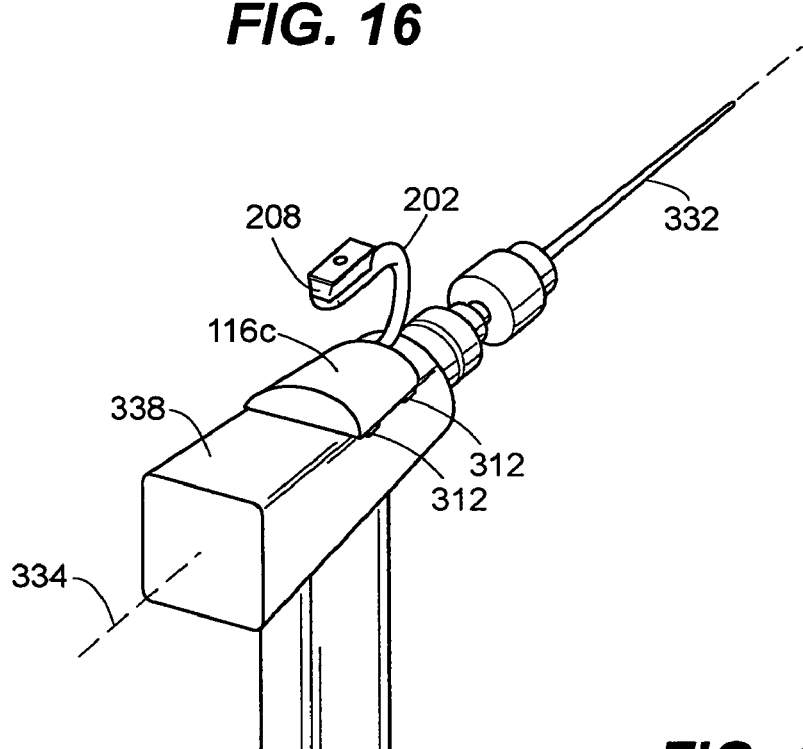
FIG. 16 is an isometric view of a surgical drill with the adapter of FIG. 14 in place.
Figure 17:
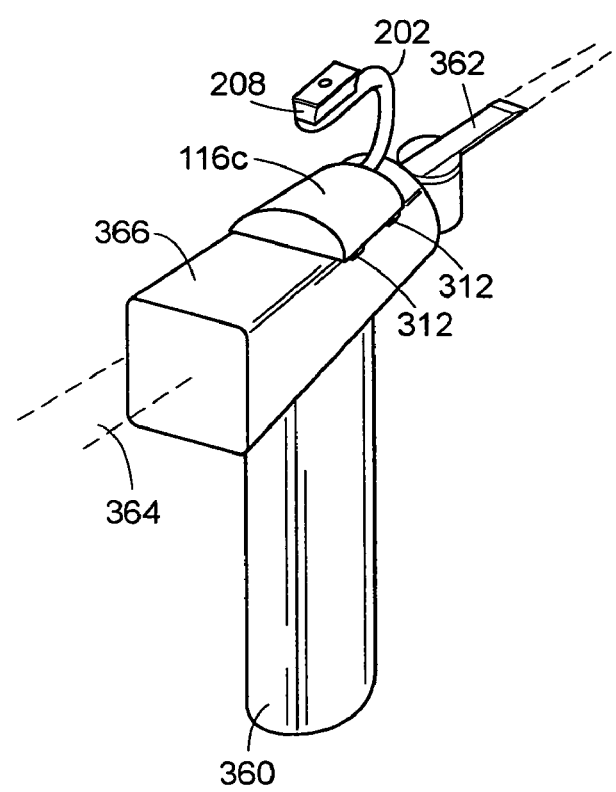
FIG. 17 is an isometric view of a surgical saw with the adapter of FIG. 14 in place.

FIGS. 16 and 17 illustrate the use of the adapter 116c in conjunction with a surgical drill 330 and a surgical saw 360. The surgical drill 330 has a drill bit 332 with an effector axis 334. As indicated in FIG. 14, the adapter 116c, shown without the attached navigation tracker for clarity, is held against a top surface 338 of the surgical drill 330. So long as the top surface 338 is co-linear with the effector axis 334, the adapter can be moved along the top surface 338 without affecting the relationship between the effector axis 334 and the adapter 116c. This tool-adapter-tracker combination can be calibrated using the method shown in FIG. 8 or a database can have sufficient information to perform the calibration without kinematic analysis of the effector axis 334. In a similar manner, a saw blade 362 has an effector plane 364. An adapter 116c is placed on a top surface 366 of the surgical saw 360. Using the method outlined in FIG. 8 above the relation of the effector plane 364 to the adapter 116c can be determined and calibrated. It is also possible to use the database method of FIG. 9 to calibrate the adapter 116c with attached tracker to the effector plane 364.

Figure 18:
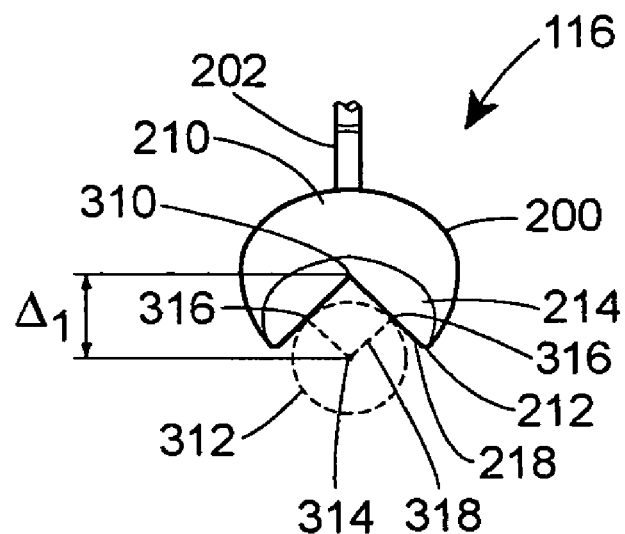
FIG. 18 is an end elevational view of the adapter similar to FIG. 4 showing the adapter relative to a surgical instrument having a circular cross section.
Figure 19:
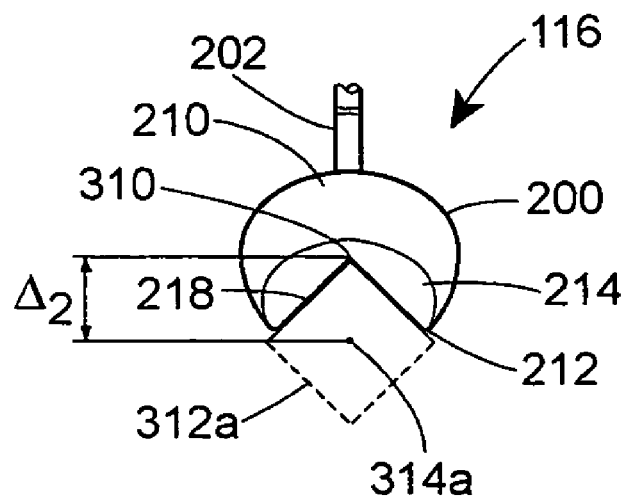
FIG. 19 is an end elevational view of the adapter similar to FIG. 4 showing the adapter relative to a surgical instrument having a square cross section.

Referring to FIGS. 18 and 19, the adapter 116 is shown associated with surgical instruments of two different cross sections relative to an apex 310 of the channel 218. FIG. 18 shows a surgical instrument 312 that has a circular cross section. The surgical instrument 312 has an instrument axis 314. The surgical instrument 312 contacts the channel 218 at two points 316 that are equidistant from the channel apex 310. The surgical instrument 312 has a radius 318 and the instrument axis 314 is a distance $\Delta_1$ from the channel apex 310. So long as the radius 318 is constant along the length of the surgical instrument 312 and the surgical instrument 312 is straight, the adapter 116 can be moved along the length of the surgical instrument 312 and the relation between the instrument axis 314 and the tracker 118 will remain constant. The adapter 116 and attached tracker are rotated around the instrument axis. The location of the instrument axis 314 will remain fixed but the location of the tracker will change. The distance between the instrument axis 314 and the tracker will remain constant. Alternatively, the instrument 312, the adapter 116 and the attached tracker can also be rotated as a unit. Either method provides the basis for the rotation calibration method described above relative to FIG. 8. The following is an example of how the database method of FIG. 9 can calculate the location of the instrument axis 312 relative to the tracker 118. The surgical navigation system 100 will have the position and orientation of the apex 310 of the adapter 116 stored in the adapter database 428 relative to the position and orientation of the navigation tracker 118 that is attached to the adapter 116. Similarly, the surgical navigation system 100 will also have the value $\Delta_1$ for the surgical instrument 312 stored in the instrument database. Using these values and the location and orientation of the navigation tracker 118, the surgical navigation system 100 can calculate the effector axis of the instrument 312 in the block 432.

In a similar manner, a surgical instrument 312a as shown in FIG. 19 has a square or rectangular cross section that fits snugly against the apex 310. Since there can be no relative movement between the instrument 312a and the V shaped channel 218, the entire combination of the instrument, the adapter and the tracker are rotated around the instrument axis 314*a* to perform the calibration as described above relative to FIG. 8. With regard to the database method of FIG. 9, the instrument 312*a* has a known square cross section as shown by the distance $\Delta_2$ from an instrument axis 314*a* to the apex 310 and is stored in the instrument database 430 as noted above. If the cross section of the instrument is not square the instrument database 430 may include other parameters to enable the surgical navigation system 100 to determine the effector axis or plane. One advantage of using a V shaped channel 218 along with a surgical instrument 312*a* having a square or rectangular cross section is that there is no relative rotation between the adapter 116 and the surgical instrument 312*a*.

The adapter of the present invention may be made from any suitable material that is dimensionally stable and capable of being sterilized at least one time. Though it may be desirable that the interface be capable of being repeatedly sterilized, it is also possible that the adapters 116 of the present invention are designed as disposable single use items, which are sterilized upon manufacture, maintained in a sterile condition until use and then discarded. Suitable plastics, which are dimensionally stable and surgically acceptable, such as polyetheretherketone (PEEK), carbon or glass fiber reinforced PEEK, polysulfone, polycarbonate, nylon and mixtures thereof, can be used. In addition, suitable metals that are acceptable for use in surgery such as surgical stainless steel, titanium, tungsten carbide and other similar surgically suitable metals can be used. In one embodiment, the adapter 116 and the channel 218 will be constructed from materials having a hard surface to prevent wearing when the surgical instrument is moved along the surface of the channel 218.

Figure 20:
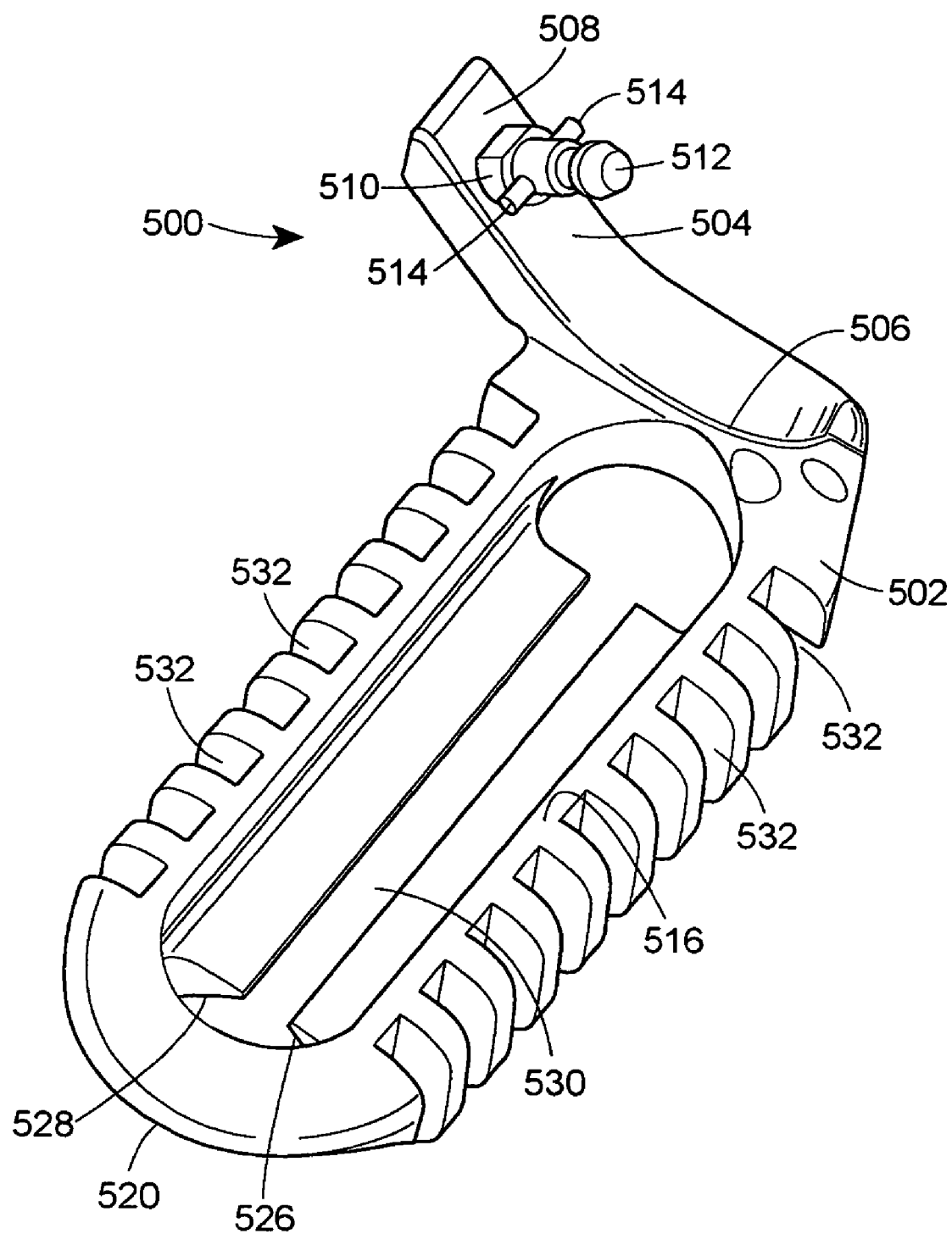
FIG. 20 is an isometric view of a further embodiment of the adapter of the present invention.
Figure 21:
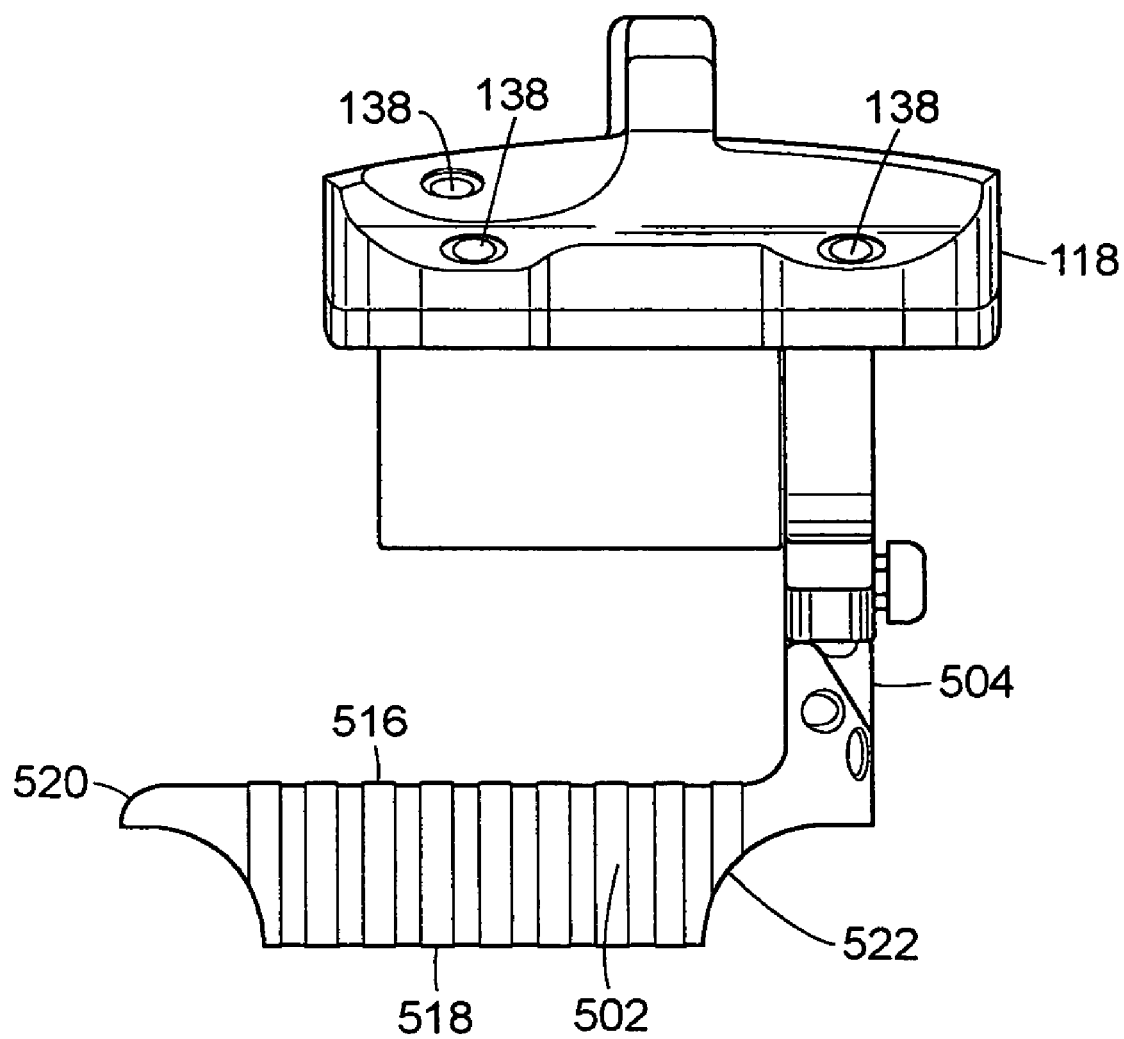
FIG. 21 is a side view of the adapter of FIG. 20 with a tracker attached.

FIGS. 20 and 21 show a further embodiment of an adapter 500. The adapter 500 has a body 502 with a connector 504 having a first end 506 attached to the body 502 and a second end 508 attached to a docking structure 510. The docking structure 510 has a center lug 512 and two pins 514 that interfit with the navigation tracker 118. The body 502 has a first side 516, a second side 518, a first end 520, and a second end 522. The second side 518 defines a geometrical feature 524. In this case, the geometrical feature is a pair of arced surfaces 526 and 528. An opening 530 between the arced surfaces 526 and 528 reduces the weight of the adapter 500. The arced surfaces 526 and 528 will fit against tools that have a circular cross section. The body 502 also has a series of cutouts 532 that will further reduce the weight of the adapter and may assist the user in grasping the adapter 500.

Figure 22:
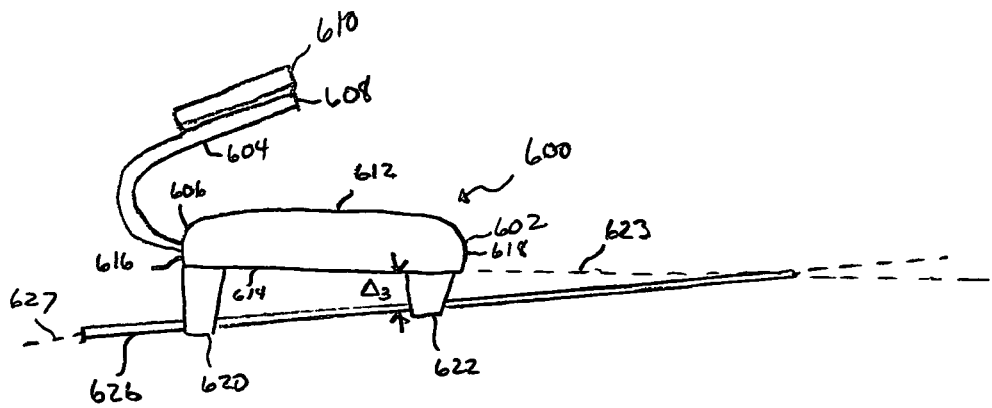
FIG. 22 is a side elevational view of a further embodiment of an adapter device showing the relation with a surgical device.
Figure 23:
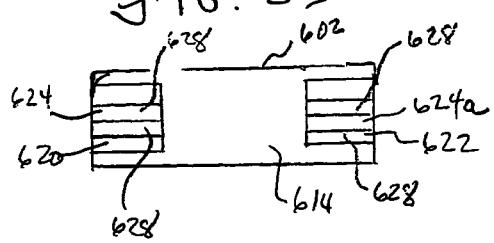
FIG. 23 is a bottom plan view of the adapter of FIG. 22.
Figure 24:
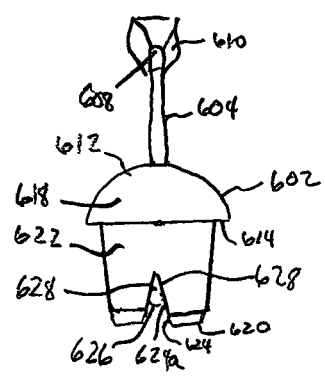
FIG. 24 is an end elevational view of the adapter of FIG. 22.

Referring to FIGS. 22-24, a further embodiment of the devices and system of the present inventions is shown. In this embodiment an adapter 600 has a body 602 and a connector 604. The connector 604 has a first end 606 and a second end 608 that is connected to a docking structure 610. The docking structure is similar to those discussed above and is capable of interfitting with a navigation tracker, such as the navigation tracker 118. The body 602 has a first side 612, a second side 614, a first end 616, and a second end 618. Two projections 620 and 622 are attached to the second side 614. In this embodiment, the second side 614 is on a plane 623. Each of the projections 620 and 622 has a V-shaped notch 624 and 624*a* to receive a surgical device 626. The surgical device 626 can be any of the surgical instruments or devices that have been discussed previously. In addition, the surgical device 626 can be an object to be placed within the patient's body, such as a shunt or stint. In one embodiment, the depth of the notches 624 and 624*a* are different to place the surgical device 626 on an angle relative to the second side 614 such that an effector axis 627 of the surgical device 626 will intersect the plane 623 approximately 70 mm from the first end 616. The notches 624 and 624*a* each have two sloping walls 628 that meet at an apex 630. The V-shaped notches 624 and 624*a* enable the adapter to be used with different sizes of surgical devices 626. The surgical device 626 will rest within the notches 624 and 624*a* against the respective walls 628. The walls 628 for each of notches 624 and 624*a* should also lie on the same plane so that the notches 624 and 624*a* are a continuation of each other. For some embodiments, it may not be necessary to allow space for a users hand between the projections 620 and 622. In this case, the two projections can be replaced by a single projection with a long notch. For particular surgical devices 626, the database will know the relative distance from the effector axis of the particular surgical device 626 to the tracking device 118 and the angle of the effector axis 627 relative to the tracking device 118. The distance from the second side 614 to the apex 630 of the notch 624, $\Delta_3$, should be large enough so that a user can get their hand between the second side 614 and the surgical device 626 to manipulate the surgical device 626, if needed.

Figure 26:
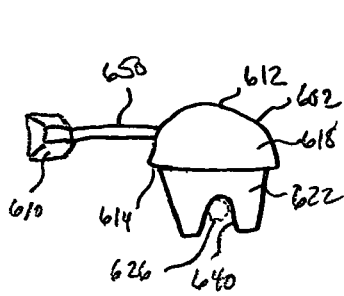
FIG. 26 is a view similar to FIG. 24 of another further embodiment of the adapter.
Figure 25:
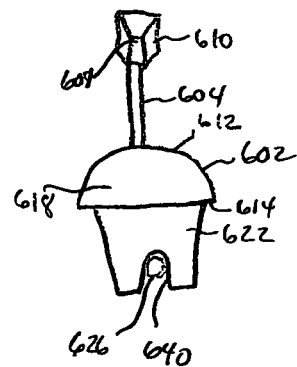
FIG. 25 is a view similar to FIG. 24 of a further embodiment of the adapter.

FIG. 25 shows a further embodiment where each projection 620 and 622 have a U-shaped notch 640. In this embodiment, the adapter will be specially constructed to work with a particular device that has a slightly smaller radius than the radius of the bottom of the U-shaped notch 640. FIG. 26 shows another embodiment where a connector 650, similar to the connector 604, projects from the body 602 90 degrees from the direction that the connector 604 projects from the body 602. This alternative arrangement can allow added flexibility for the user to manipulate the surgical device 626 relative to the tracking device 118.

Figure 27:
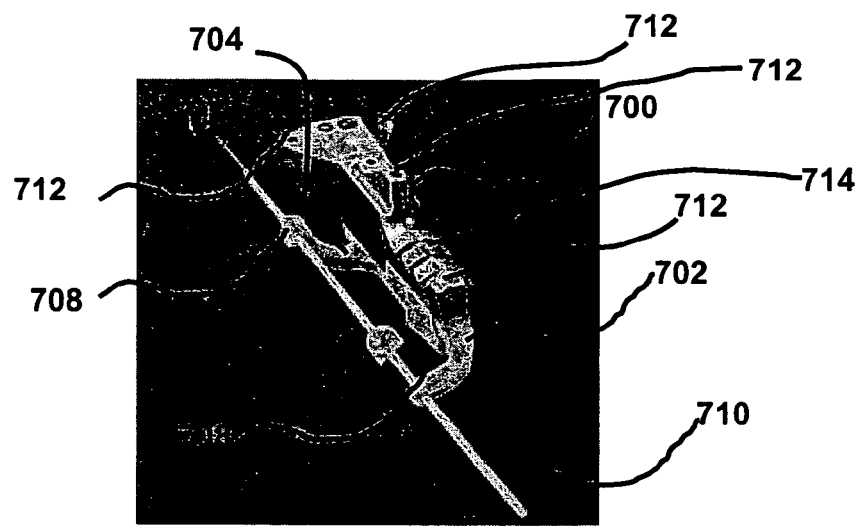
FIG. 27 is a perspective view of one embodiment of a tracking device with integral projections.

FIG. 27 shows a further embodiment where a tracking device 700 has integral projections 702 and 704. The projections 702 and 704 are directly attached to a body 706 of the tracking device 700 and both are space apart and extend to the side of the tracking device 700 a sufficient distance to allow a user to place their hand within the space between the two projections 702 and 704. The two projections 702 and 704 have similar U-shaped notches 708 to receive a surgical device 710, such as the shunt as shown in FIG. 27. The tracking device 700 has integral LEDs 712 that are similar to those described above. In addition, the tracking device 700 also has three switches 714 that are useful to control the surgical navigation system.

Figure 28:
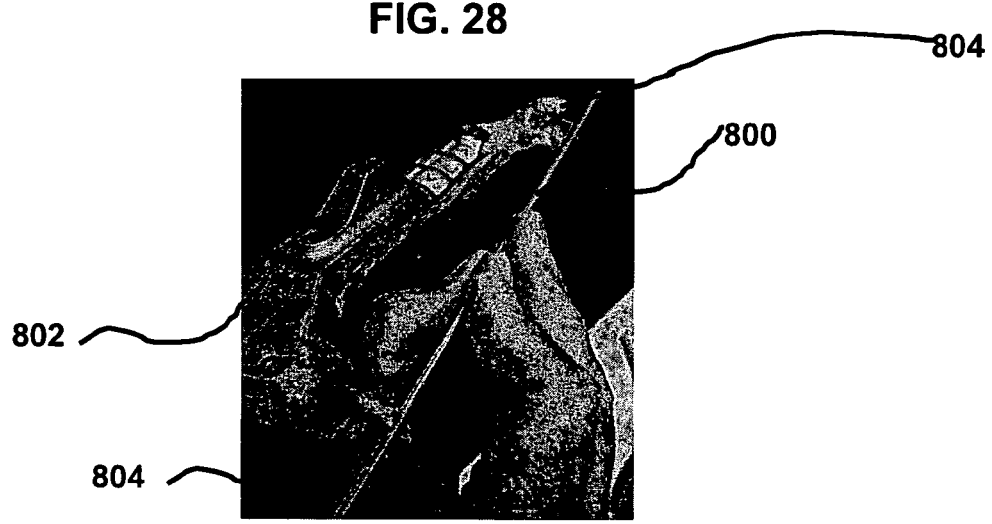
FIG. 28 is a detailed view of a further embodiment of a tracking device similar to FIG. 27 showing the placement of a surgical device in the grooves.
Figure 29:
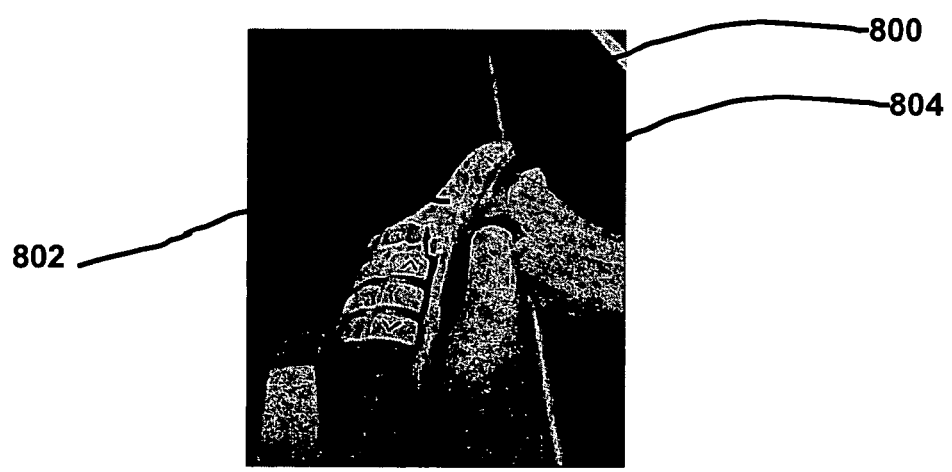
FIG. 29 is a detailed view of the device of FIG. 28 showing the user manipulating the surgical device relative to the tracking device.

FIGS. 28 and 29 show a user manipulating a surgical device 800 relative to a further embodiment of an integral tracking device 802. The user can place the surgical device 800 into each notch 804 to guide the surgical device to the proper location. In addition, because the surgical device is not held firmly within the notches 804, the user can manipulate the surgical device as needed as shown in FIG. 28.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications that come within the scope of the appended claims are reserved.

We claim:

1. A system for orienting a surgical device, comprising:
    a surgical navigation system having a display unit;
    a navigation tracker having a body including a geometrical feature defining an unobstructed axial channel extending along the body between opposite open ends and capable of being movably coupled to a surgical device having an effector axis, the navigation tracker capable of being tracked by the navigation system, wherein there is a known relation between the navigation tracker and the effector axis when the surgical device is disposed in and moving longitudinally along the axial channel;

a first circuit adapted to calculate an orientation of the effector axis of the surgical device from the known relation between the navigation tracker and the effector axis while the surgical device is movably coupled in and moving longitudinally along the axial channel; and a second circuit for displaying the orientation of the effector axis of the surgical device on a display unit.

2. The system of claim 1 wherein a hand can easily hold the navigation tracker in place relative to the surgical device.

3. The system of claim 1 wherein the system further includes a database of the known relations of the navigation tracker to the effector axis of the surgical device, and wherein the database provides the known relation to the first circuit.

4. The system of claim 1 wherein the navigation tracker is an optical tracking device.

5. The system of claim 4 wherein the optical tracking device includes infrared LED's.

6. The system of claim 1 wherein the navigation tracker does not include a mechanical locking device for coupling the surgical device.

7. The system of claim 1 wherein the body has a first side, a second side, and the geometrical feature is on the second side capable of being movably coupled with respect to the surgical device.

8. The system of claim 7 wherein the geometrical feature is shaped to allow a reproducible alignment between the navigation tracker and the effector axis.

9. The system of claim 7 wherein the geometrical feature comprises a V-shaped channel.

10. The system of claim 7 wherein the geometrical feature is a series of spaced lugs on the second side.

11. The system of claim 7 wherein the geometrical feature comprises two notches that are spaced apart along the axial channel.

12. The system of claim 7 wherein the second side is comprised of a hard surface to prevent wearing when held against the surgical device.

13. The system of claim 7 wherein the body includes at least two geometrical features projecting outwardly from the body, wherein the geometrical features are spaced apart and aligned along the effector axis, and wherein the geometrical features define the axial channel.

14. The system of claim 13 wherein the geometrical features include V-shaped notches.

15. The system of claim 13 wherein the geometrical features include U-shaped notches.

16. A method for orienting a surgical device, the method comprising the steps of:

coupling by a user's hand a navigation tracker to a surgical device that has an effector axis in a movable manner using a geometrical feature associated with the navigation tracker, wherein the navigation tracker is capable of communicating with a navigation system, and wherein there is a known relation between the navigation tracker and the effector axis;

calculating orientation data for the effector axis of the surgical device from the known relation between the navigation tracker and the effector axis, wherein the calculating step is performed while the surgical device is moving longitudinally along the geometrical feature and movably coupled to the navigation tracker by the user's hand; and displaying the orientation data for the effector axis of the surgical device on a display unit of the navigation system so that when the surgical device is used with the navigation system, the orientation of the effector axis of the surgical device can be tracked by the navigation system.

17. The method of claim 16 wherein a hand can easily hold the navigation tracker in place relative to the surgical device.

18. The method of claim 16 including the additional step of providing a database of the known relations of the navigation tracker to the effector axis, the database being utilized to calculate the orientation of the surgical device.

19. The method of claim 16, wherein the navigation tracker includes a body and the geometrical feature defines an unobstructed axial channel extending along the body, and wherein the step of calculating is performed while the surgical device is movably coupled in the entire length of the axial channel.

20. The method of claim 16 wherein the navigation tracker is an optical tracking device.

21. The method of claim 20 wherein the optical tracking device includes infrared LED's.

22. The method of claim 16 wherein the navigation tracker has a body with a first side and a second side, wherein the geometrical feature is located on the second side.

23. The method of claim 22 wherein the second side is comprised of a hard surface to prevent wearing when held against the surgical device.

24. The method of claim 22 wherein the geometrical feature comprises an axial channel extending along the second side of the body, wherein the axial channel is unobstructed between opposite open ends.

25. The method of claim 24 wherein the geometrical feature comprises a V-shaped channel.

26. The method of claim 24 wherein the geometrical feature is a series of lugs on the second side.

27. The method of claim 24 wherein the geometrical feature comprises two notches that are spaced apart along the effector axis.

28. The method of claim 24 wherein the body includes at least two geometrical features projecting from the second side of the body, wherein the geometrical features are spaced apart and aligned along the effector axis, and wherein the geometrical features define the axial channel.

29. The method of claim 28 wherein the geometrical features comprise aligned V-shaped notches.

30. The method of claim 28 wherein the geometrical features comprise aligned U-shaped notches.

* * * * *